United States Patent [19]  
Baird et al.

[11] 4,081,435  
[45] Mar. 28, 1978

[54] DISPERSE AZO DYESTUFFS DERIVED FROM A 3-AMINO-7-AZABENZ-2,1-ISOTHIAZOLE DIAZO COMPONENT

[75] Inventors: David Boyd Baird; Brian Ribbons Fischwick; James Stanley Campbell; Peter Smith, all of Manchester, England

[73] Assignee: Imperial Chemical Industries Limited, Great Britain

[21] Appl. No.: 727,384

[22] Filed: Sep. 27, 1976

[30] Foreign Application Priority Data

Oct. 27, 1975  United Kingdom .............. 44132/75

[51] Int. Cl.² .................... C09B 29/08; C09B 29/26
[52] U.S. Cl. ............................ 260/156; 260/294.8 C
[58] Field of Search ................ 260/156, 294.8 C, 158

[56] References Cited  
U.S. PATENT DOCUMENTS 3,936,435  2/1976  Clark ................................. 260/156 X  
3,943,121  3/1976  Maner et al. ..................... 260/156 X Primary Examiner—Charles F. Warren  
Attorney, Agent, or Firm—Cushman, Darby & Cushman

[57] ABSTRACT

The disperse monoazo dyestuffs, free from sulphonic acid groups, which are of the formula:

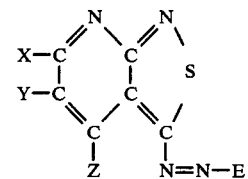

wherein
X is hydrogen, alkyl, substituted alkyl, aryl, substituted aryl, $-NR^1R^2$, $-SR_3$, chlorine, bromine $-OR^3$ or $-SO_2R^3$;
Z is hydrogen, alkyl, substituted alkyl, aryl or substituted aryl;
Y is hydrogen, nitro, cyano, $-COOR^3$, $-COR^3$, $-CONR^1R^2$, $-SO_2R^3$ or $-SO_2NR^1R^2$;
E is the residue of a coupling component;
$R^1$ is hydrogen, alkyl or aryl;
$R^2$ is hydrogen or alkyl; and
$R^3$ is alkyl or aryl, a process for the manufacture of the said dyestuffs, and their use for coloring synthetic textile materials.

2 Claims, No Drawings

DISPERSE AZO DYESTUFFS DERIVED FROM A 3-AMINO-7-AZABENZ-2,1-ISOTHIAZOLE DIAZO COMPONENT

This invention relates to disperse monoazo dyestuffs which are valuable for colouring synthetic textile materials.

According to the invention there are provided the disperse monoazo dyestuffs, free from sulphonic acid groups, which are of the formula:

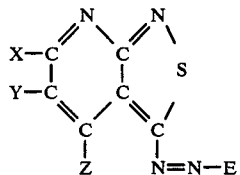

wherein

X is hydrogen, alkyl, substituted alkyl, aryl, substituted aryl, $-NR^1R^2$, $-SR^3$, chlorine, bromine, $-OR^3$ or $-SO_2R^3$;

Z is hydrogen, alkyl, substituted alkyl, aryl or substituted aryl;

Y is hydrogen, nitro, cyano, $-COOR^3$, $-COR^3$, $-CONR^1R^2$, $-SO_2R^3$ or $-SO_2NR^1R^2$;

E is the residue of a coupling component;

$R^1$ is hydrogen, alkyl or aryl;

$R^2$ is hydrogen or alkyl; and $R^3$ is alkyl or aryl.

More specifically, the invention provides a disperse monoazo dyestuff free from sulphonic acid groups which is of the formula:

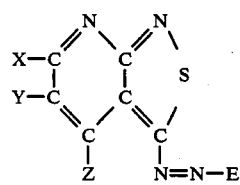

wherein

X is selected from hydrogen, lower alkyl, $-NH$ lower alkyl, lower alkylthio, lower alkoxy and lower alkylsulphonyl;

Z is selected from hydrogen, lower alkyl and phenyl;

Y is selected from hydrogen, nitro and cyano; and E is the residue of a coupling component selected from coupling components of the acylacetarylamide, pyrazolone, aminopyrazole, phenol, naphthol, 2:6-dihydroxypyridine and arylamine series.

Still more specifically, the invention provides a disperse monoazo dyestuff which is of the formula:

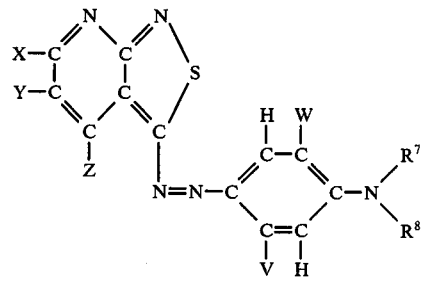

wherein

X is selected from hydrogen, lower alkyl, $-NH$ lower alkyl, lower alkylthio, lower alkoxy and lower alkylsulphonyl;

Z is selected from hydrogen, lower alkyl and phenyl;

Y is selected from hydrogen, nitro and cyano;

W is selected from hydrogen, lower alkyl and lower alkoxy;

V is selected from hydrogen, lower alkyl, lower alkoxy, chlorine, bromine, $-NHCOT^2$ and $-NHSO_2T^3$, wherein $T^3$ is lower alkyl, and $T^2$ is selected from hydrogen, lower alkyl, lower alkoxy and amino; and $R^7$ and $R^8$ are each independently selected from hydrogen, lower alkyl, lower alkoxy lower alkoxy carbonyl lower alkyl, lower alkylcarbonyloxy lower alkyl, cyano lower alkyl, lower alkoxycarbonyl lower alkyl, phenyl lower alkyl, cyano lower alkoxycarbonyl lower alkyl, hydroxy lower alkyl, benzoyloxy lower alkyl, phenyl and cyclohexyl.

Throughout this Specification the terms "lower alkyl" and "lower alkoxy" are used to denote alkyl and alkoxy radicals respectively containing from 1 to 4 carbon atoms.

It is preferred that X is hydrogen or lower alkyl, Y is nitro, and Z is hydrogen.

The alkyl radicals represented by X, Z, $R^1$, $R^2$ and $R^3$ are preferably lower alkyl radicals such as methyl, ethyl n-propyl and n-butyl. The substituted alkyl radicals represented by X and Z are preferably substituted lower alkyl radicals for example lower alkoxy lower alkyl such as β-methoxyethyl and lower alkylcarbonyl lower alkyl such as β-acetylethyl. The aryl radicals represented by X, Z, $R^1$ and $R^3$ are preferably phenyl radicals. The substituted aryl radicals represented by X and Z are preferably substituted phenyl radicals such as tolyl, xylyl, anisyl, chlorophenyl, bromophenyl and nitrophenyl.

The residue of the coupling component represented by E can be the residue of any of the series of coupling components which couple with diazo compounds, such as the residue of a coupling component of the acylacetarylamide, pyrazolone, aminopyrazole, phenol, naphthol or 2:6-dihydroxypyridine series. More especially E is the residue of a coupling component of th aromatic series which couples by virtue of the presence of an optionally substituted amino group, such as the residue of a coupling component of the 1-naphthylamine series, and above all the residue of a coupling component of the aniline series which couples in para position to an optionally substituted amino group.

The residue of the coupling component represented by E is preferably of the formula:

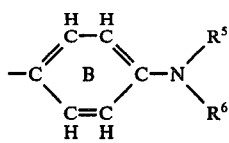

wherein $R^5$ and $R^6$ each independently represent a hydrogen atom or an optionally substituted hydrocarbon radical, especially an optionally substituted lower alkyl radical, and the benzene ring B can contain additional substituents or form part of an optionally further substituted naphthalene or quinoline ring.

E especially represents a radical of the formula:

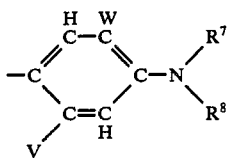

Wherein W is hydrogen, lower alkyl or lower alkoxy, V is hydrogen, lower alkyl, lower alkoxy, chlorine, bromine or acylamino, in particular an acylamino group of the formula $—NHCOT^2$ or $—NHSO_2T^3$, wherein $T^2$ is hydrogen, alkyl especially lower alkyl, aryl, amino or aminoalkyl, $T^3$ is optionally substituted lower alkyl or aryl, $R^7$ is hydrogen or an optionally substituted alkyl especially lower alkyl radical, and $R^8$ is hydrogen or an optionally substituted alkyl especially lower alkyl, or optionally substituted aryl or cycloalkyl radical.

As examples of the optionally substituted lower alkyl radicals represented by $R^7$ and $R^8$ there may be mentioned hydroxy lower alkyl such as β-hydroxyethyl, β- or γ-hydroxypropyl and δ-hydroxybutyl, lower alkoxy lower alkyl such as β-(methoxy or ethoxy) ethyl and γ-methoxypropyl, cyano lower alkyl such as β-phenylethyl, carboxy lower alkyl such as β-carboxyethyl and δ-carboxybutyl, lower alkoxy carbonyl lower alkyl such as β-methoxycarbonylethyl, hydroxy lower alkoxy lower alkyl such as β-(β'-hydroxyethoxy)ethyl, lower alkoxy lower alkoxy lower alkyl such as β-(β'-methoxyethoxy)ethyl, lower alkoxy lower alkoxy carbonyl lower alkyl such as β-(β'-methoxyethoxycarbonyl)ethyl, acyloxy lower alkyl in particular lower alkylcarbonyloxy lower alkyl such as β-acetoxyethyl and δ-acetoxybutyl, chloro lower alkyl such as γ-chloropropyl, lower alkoxycarbonyl lower alkyl such as β-ethoxycarbonyloxyethyl, and benzoyloxy lower alkyl such as β-benzoyloxyethyl.

According to a further feature of the invention there is provided a process for the manufacture of the azo dyestuffs as hereinbefore defined which comprises diazotising an amine of the formula:

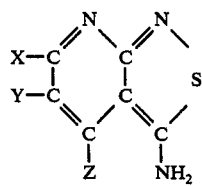

and coupling the resulting diazo compound with a coupling component of the formula — E—H, wherein E, X, Y and Z have the meanings stated, the amine and coupling component being free from sulphonic acid groups.

The process of the invention can be conveniently carried out by adding sodium nitrite to a solution or dispersion of the amine in a strong inorganic acid or an aqueous solution thereof, or by stirring the amine with nitrosylsulphuric acid, and adding the resulting solution or dispersion of the diazo component to a solution of the coupling component in water or in a mixture of water and a water-miscible organic liquid, if necessary adjusting the pH of the mixture to facilitate the coupling reaction, and finally isolating the resulting dyestuff by conventional methods.

The amines of the above formula can themselves be obtained by, for example, treating a solution of the appropriate compound of the formula:

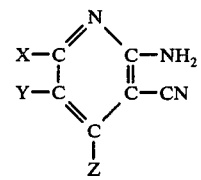

in a basic organic liquid with hydrogen sulphide and subsequently oxidising with hydrogen peroxide.

As specific examples of the said amines there may be mentioned 3-amino-5-nitro-6-methyl-7-azabenz-2:1-isothiazole (3-amino-5-nitro-6-methylpyrido[2,3-c]isothiazole), 3-amino-5-methoxycarbonyl-6-methyl-7-azabenz-2:1-isothiazole and 3-amino-5-nitro-7-azabenz-2:1-isothiazole.

As examples of the said coupling components there may be mentioned acylacetarylamides such as acetoacetanilide and acetoacet-2:5-dimethoxyanilide; aminopyrazolones such as 1-phenyl-3-methyl-5-aminopyrazole; pyrazolones such as 1:3-dimethyl-5-pyrazolone but more particularly 1-phenyl-3-(methyl, carbonamido or carbomethoxy)-5-pyrazolones in which the phenyl radical is optionally substituted by for example methyl, methoxy, ethoxy, chlorine, bromine, nitro, sulphonamido or acetylamino; 2:6-dihydroxypyridines such as 3-cyano-4-methyl-2:6-dihydroxypyridine and 1-ethyl-3-cyano-4-methyl-6-hydroxypyrid-2-one; phenols such as o-cresol, resorcinol and 3-acetylaminophenol; naphthols such as β-naphthol; but more especially arylamines of the naphthylamine series such as 1-naphthylamine, and more particularly of the aniline series such as 2:5-dimethoxyaniline, N:N-diethylaniline, N:N-di(β-hydroxyethyl)-m-toluidine, N:N-di(β-cyanoethyl)-aniline, N-ethyl-N-(β-ethoxyethyl)aniline, N:N-di(β-carbomethoxyethyl)-m-toluidine, N-[β-(β'-methoxyethoxycarbonyl)ethyl]-m-toluidine, 2-methoxy-5-acetylamino-N-[β-(β'-methoxyethoxycarbonyl)ethyl]aniline, N:N-di(β-acetoxyethyl)-m-toluidine, N-ethyl-N-(β-cyanoethyl)aniline, N-ethyl-N-(δ-acetoxybutyl)aniline and N-ethyl-N-benzyl-m-toluidine.

The azo dyestuffs of the invention are valuable for colouring synthetic textile materials in particular secondary cellulose acetate and cellulose triacetate textile materials, polyamide textile materials such as polyhexamethylene adipamide textile materials, and, above all, aromatic polyester textile materials such as polyethylene terephthalate textile materials. Such materials can be in the form of filaments, fibres or woven or knitted materials.

The said azo dyestuffs can be applied to the synthetic textile materials by methods which are conventionally employed in applying disperse dyestuffs to such textile materials. Thus the dyestuffs in the form of aqueous dispersions can be applied by dyeing, padding or printing processes using the conditions and other additives which are conventionally used in carrying out such processes. Alternatively the said dyestuffs can be applied to synthetic textile materials by solvent methods of dyeing, for example by applying a solution or dispersion of the dyestuff in perchloroethylene optionally containing a minor amount of water to the textile material preferably at elevated temperature.

When applied to synthetic textile materials the azo dyestuffs of the invention give yellow to green colourations which have excellent fastness to light and to wet and to dry treatments. The said dyestuffs also have excellent build-up properties on synthetic textile materials, particularly aromatic polyester textile materials, thus enabling heavy depths of shade to be readily obtained. Alternatively the said dyestuffs can be used for the mass colouration of synthetic polymers which are subsequently to be converted into fibres or filaments. The said dyestuffs can also be applied to synthetic textile materials by the process of transfer colouring printing optionally at reduced air pressures or under wet or humid conditions.

The invention is illustrated but not limited by the following Examples in which the parts and percentages are by weight.

EXAMPLE 1

0.76 Part of sodium nitrite is added to 5 parts of sulphuric acid and the mixture is heated to 70° C then cooled to 5° C. A mixture of 1.4 parts of propionic acid and 8.6 parts of acetic acid is added, the temperature being allowed to rise to 15° C. The mixture is then cooled to 0° C., 2.2 parts of 3-amino-5-nitro-6-methyl-7-azabenz-2:1-isothiazole are added followed by 10 parts of the same mixture of acetic and propionic acids. The mixture is stirred for 75 minutes at 5° C., 10 parts of the same mixture of acids added, and the mixture stirred for 75 minutes at 5° C., 10 parts of the same mixture of of acids added, and the mixture stirred for a further hour at 5° C Urea is added to destroy any residual nitrous acid, and the mixture is then slowly added to a solution of 3.1 parts of 2-methoxy-5-acetylamino-N-[β-(β'-methoxyethoxycarbonyl)ethyl]aniline in 50 parts of water, 6 parts of a 2N aqueous solution of hydrochloric acid and 250 parts of ice. The pH of the mixture is then raised to 4 by the addition of sodium acetate, and the precipitated dyestuff is filtered off, washed with water and dried.

When dispersed in aqueous medium the dyestuff dyes polyethylene terephthalate textile materials in bluish-green shades of excellent fastness properties.

By replacing the 3.1 parts of the above coupling component by an equivalent amount of N:N-diethylaniline a dyestuff is obtained which gives blue shades on polyethylene terephthalate textile materials.

The 3-amino-5-nitro-6-methyl-7-azabenz-2:1-isothiazole was itself obtained by heating 2-chloro-3-cyano-5-nitro-6-methylpyridine with a mixture of methanol and a concentrated ammonium hydroxide solution, passing hydrogen sulphide through a solution of the resulting 2-amino-3-cyano-5-nitro-6-methylpyridine in a mixture of pyridine and triethylamine, isolating the 2-amino-3-thiocarbonamido-5-nitro-6-methylpyridine, and finally treating a solution of this compound in acetic acid with 100 volume hydrogen peroxide solution.

EXAMPLE 2

2.1 Parts of 3-amino-5-nitro-6-methyl-7-azabenz-2:1-isothiazole are added to 20 parts of a solution of nitrosylsulphuric acid (which had been prepared by dissolving 118 parts of sodium nitrite in 2400 parts of sulphuric acid at 60° C, cooling and diluting with 450 parts of acetic acid and 70 parts of propionic acid) the temperature being maintained at 0° to 5° C by external cooling. The mixture is stirred for 1½ hours at 0° C, and sufficient urea then added to destroy any residual nitrous acid. The resulting solution of the diazo compound is added to a mixture of 2.1 parts of 3-acetylamino-N:N-diethylaniline, 10 parts of a concentrated aqueous solution of hydrochloric acid and 200 parts of ice, and the pH of the mixture then raised to 4 by the addition of sodium acetate. The mixture is stirred for 1 hour and the precipitated dyestuff is filtered off, washed with water, and dried.

When dispersed in aqueous medium the dyestuff dyes aromatic polyester textile materials in turquoise shades.

The following Table I gives further examples of the dyestuffs of the invention which are obtained when the 2.1 parts of 3-acetylamino-N:N-diethylaniline used in Example 2 are replaced by equivalent amounts of the coupling components listed in the second column of the following Table; the shades obtained from the said dyestuffs being given in the third column of the Table.

Table I

| Example | Coupling Component | Shade |
|---|---|---|
| 3 | N:N-di(β-acetoxyethyl)aniline | Reddish-blue |
| 4 | 3-chloro-N:N-di(β-acetoxyethyl)aniline | Bluish-violet |
| 5 | 3-acetylamino-N:N-di(β-acetoxyethyl)aniline | Greenish-blue |
| 6 | 3-propionylamino-N:N-di(β-acetoxyethyl)aniline | " |
| 7 | 3-methoxy-N:N-di(β-acetoxyethyl)aniline | Blue |
| 8 | 2:5-dimethyl-N-(β-cyanoethyl)aniline | Bluish-violet |
| 9 | 2-chloro-5-methoxy-N-(β-methoxycarbonylethyl)aniline | Reddish-blue |
| 10 | 2-methoxy-5-chloro-N-(β-ethoxycarbonylethyl)aniline | " |
| 11 | 2:5-dimethoxy-N:N-di(β-acetoxyethyl)aniline | Bluish-green |
| 12 | 3-methyl-N:N-di(β-methoxycarbonylethyl)aniline | Blue |
| 13 | N:N-di(β-methoxycarbonylethyl)aniline | Reddish-blue |
| 14 | 3-bromo-N:N-di(β-methoxycarbonylethyl)aniline | Bluish-violet |
| 15 | 3-acetylamino-N:N-di(β-methoxycarbonylethyl)aniline | Greenish-blue |
| 16 | 2-methoxy-5-methyl-N-(β-methoxycarbonylethyl)aniline | " |

Table I-continued

| Example | Coupling Component | Shade |
|---|---|---|
| 17 | 3-methyl-N-methyl-N-(β-methoxycarbonylethyl)aniline | Blue |
| 18 | N-ethyl-N-(β-methoxycarbonylethyl)aniline | " |
| 19 | N-ethyl-N-(β-ethoxycarbonylethyl)aniline | " |
| 20 | N-ethyl-N-(β-n-butoxycarbonylethyl)aniline | " |
| 21 | N-ethyl-N-[β-(β'-methoxyethoxycarbonyl)ethyl]aniline | Reddish-blue |
| 22 | N-ethyl-N-(β-acetoxyethyl)aniline | Blue |
| 23 | N-ethyl-N-benzylaniline | " |
| 24 | N-ethyl-N-(β-phenylethyl)aniline | " |
| 25 | 3-methyl-N:N-di-(β-methoxycarbonyloxyethyl)aniline | " |
| 26 | N-ethyl-N-(β-cyanomethoxycarbonylethyl)aniline | " |
| 27 | 3-methyl-N:N-di(β-propionyloxyethyl)aniline | " |
| 28 | N-ethyl-N-(β-cyanoethyl)aniline | " |
| 29 | N-(β-cyanoethyl)-N-(β-acetoxyethyl)aniline | Bluish-violet |
| 30 | N-(β-cyanoethyl)-N-(β-ethoxycarbonyl-aniline | " |
| 31 | 3-acetylamino-N-(β-cyanoethyl)-N-(β-methoxycarbonylethyl)aniline | Blue |
| 32 | 3-acetylamino-N-(β-cyanoethyl)-N-[β-(β'-methoxyethoxycarbonyl)ethyl]aniline | " |
| 33 | 3-acetylamino-N-ethyl-N-(β-methoxycarbonylethyl)aniline | Greenish-blue |
| 34 | 3-acetylamino-N:N-di(β-hydroxyethyl)aniline | Blue |
| 35 | 2-methoxy-5-acetylamino-N-[β-(β'-ethoxyethoxycarbonyl)ethyl]aniline | Bluish-green |
| 36 | 3-acetylamino-N-[β-(β'-ethoxyethoxycarbonyl)ethyl]aniline | " |
| 37 | N:N-di(β-hydroxyethyl)aniline | Greenish-blue |
| 38 | N-ethyl-N-(β-hydroxyethyl)aniline | " |
| 39 | 3-methylsulphonylamino-N:N-di-(β-acetoxyethyl)aniline | " |
| 40 | 3-(p-toluenesulphonylamino)-N:N-di-(β-acetoxyethyl)aniline | " |
| 41 | 3-methyl-N:N-di(β-hydroxyethyl)aniline | " |
| 42 | 3-methyl-N-ethyl-N-(β-hydroxyethyl)aniline | " |
| 43 | 3-acetylamino-N:N-di(β-ethoxycarbonylethyl)aniline | " |
| 44 | 3-acetylamino-N:N-di(β-acetoxyethyl)aniline | " |
| 45 | 3-ethoxycarbonylamino-N:N-di(β-acetoxyethyl)aniline | " |
| 46 | 3-benzoylamino-N:N-di(β-acetoxyethyl)aniline | " |
| 47 | 3-chloro-N:N-di(β-hyroxyethyl)aniline | Blue |
| 48 | 2-methoxy-5-methylaniline | " |
| 49 | N:N-dimethylaniline | Reddish-blue |
| 50 | 2:5-dimethoxyaniline | Greenish-blue |
| 51 | 3-acetylaminoaniline | Blue |
| 52 | 3-ureido-N:N-di(β-acetoxyethyl)aniline | Greenish-blue |
| 53 | 3-formylamino-N:N-di(β-methoxycarbonylethyl)aniline | " |
| 54 | 3-methyl-N:N-di(β-acetoxyethyl)aniline | Blue |
| 55 | 2-methoxy-5-acetylaminoaniline | Greenish-blue |
| 56 | 3-acetylamino-N:N-di(n-butyl)aniline | " |
| 57 | 3-methyl-N:N-diethylaniline | " |
| 58 | N-(β-cyanoethyl)-N-(β-benzoyloxyethyl)aniline | Bluish-violet |
| 59 | 2-ethoxy-5-acetylamino-N-(β-n-butoxycarbonylethyl)aniline | Bluish-green |

EXAMPLE 60

In place of the 2.1 parts of 3-amino-5-nitro-6-methyl-7-azabenz-2:1-isothiazole used in Example 2 there are used 2.0 parts of 3-amino-5-nitro-7-azabenz-2:1-isothiazole whereby a dyestuff is obtained which dyes aromatic polyester textile materials in bluish-green shades.

In place of the 3-acetylamino-N:N-diethylaniline which is used as the coupling component in Example 60 there are used equivalent amounts of 3-methyl N-ethyl-N-(β-acetoxyethyl)aniline or of the coupling components listed in Examples 15, 18, 22, 23, 28, 29, 31, 35 and 54 of Table I whereby dyestuffs are obtained which dye aromatic polyester textile materials in respectively greenish-blue, greenish blue, blue, blue, blue, reddish blue, reddish-blue, blue, green and blue shades.

Tables II and III give further Examples of the dyestuffs of the invention which are obtained by diazotising the amines listed in the second column of the Tables and coupling with the coupling components listed in the third column of the Tables using methods similar to that described in Example 1. The fourth column of the Tables gives the shades obtained when the dyestuffs are applied to aromatic polyester textile materials.

Table II

| Example | Amine | Coupling Component | Shade |
|---|---|---|---|
| 61 | 3-amino-5-nitro-7-azabenz-2:1-isothiazole | N-phenylmorpholine | Blue |
| 62 | " | N-phenylpyrrolidine | " |
| 63 | " | N:N-diethyl-p-toluidine | Green |
| 64 | " | 1-phenyl-3-methyl-5-pyrazolone | Orange |
| 65 | " | N-($\beta$-hydroxyethyl)-1-naphthylamine | Bluish-green |
| 66 | " | 1-ethyl-3-cyano-4-methyl-6-hydroxypyrid-2-one | Orange |
| 67 | " | acetoacetanilide | Yellow |
| 68 | " | 1-phenyl-3-methyl-5-aminopyrazole | Red |
| 69 | " | resorcinol | Orange |
| 70 | 3-amino-5-nitro-6-methyl-7-azabenz-2:1-isothiazole | phenol | Yellow |
| 71 | " | $\beta$-naphthol | Orange |
| 72 | " | 3-cyano-4-methyl-2:6-dihydroxypyridine | " |
| 73 | " | N-ethyldiphenylamine | Blue |
| 74 | " | N-ethyl-N-cyclohexylaniline | Greenish-blue |
| 75 | " | N-($\beta$-cyanoethyl)-1:2:3:4-tetrahydroquinoline | Blue |

Table III

| Example | Amine | Coupling Component | Shade |
|---|---|---|---|
| 76 | 3-amino-7-azabenz-2:1-isothiazole | N-ethyl-N-($\beta$-methoxycarbonylethyl)aniline | Violet |
| 77 | " | 2-methoxy-5-acetylamino-N-[$\beta$-($\beta'$-methoxyethoxycarbonyl)ethyl]aniline | Blue |
| 78 | 3-amino-4:6-dimethyl-7-azabenz-2:1-isothiazole | N:N-di($\beta$-acetoxyethyl)-m-toluidine | Violet |
| 79 | 3-amino-5-cyano-6-methoxy-7-azabenz-2:1-isothiazole | " | Bluish-violet |
| 80 | 3-amino-5-cyano-6-methylthio-7-azabenz-2:1-isothiazole | " | " |
| 81 | 3-amino-5-cyano-6-methylsulphonyl-7-azabenz-2:1-isothiazole | " | " |
| 82 | 3-amino-5-cyano-7-azabenz-2:1-isothiazole | " | " |
| 83 | 3-amino-4-phenyl-5-cyano-6-chloro-7-azabenz-2:1-isothiazole | " | " |
| 84 | 3-amino-6-phenyl-7-azabenz-2:1-isothiazole | " | Violet |
| 85 | 3-amino-4-methyl-6-ethylamino-7-azabenz-2:1-isothiazole | " | " |

We claim:

1. A disperse monoazo dyestuff free from sulphonic acid and fiber-reactive groups which is of the formula:

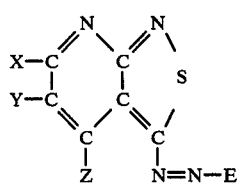

wherein
X is selected from hydrogen, lower alkyl, —NH lower alkyl, lower alkylthio, lower alkoxy and lower alkylsulphonyl;
Z is selected from hydrogen, lower alkyl and phenyl;
Y is selected from hydrogen, nitro and cyano; and
E is the residue of a coupling component selected from coupling components of the acylacetarylamide, pyrazolone, aminopyrazole, phenol, naphthol, 2:6-dihydroxypyridine and arylamine series.

2. A disperse monoazo dyestuff as claimed in claim 1 which is of the formula:

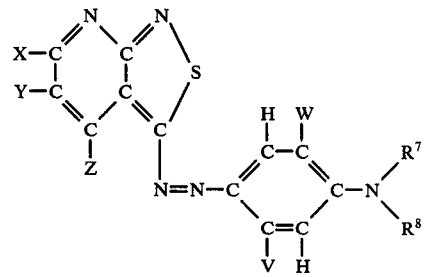

wherein
X is selected from hydrogen, lower alkyl, —NH lower alkyl, lower alkylthio, lower alkoxy and lower alkylsulphonyl;
Z is selected from hydrogen, lower alkyl and phenyl;
Y is selected from hydrogen, nitro and cyano;
W is selected from hydrogen, lower alkyl and lower alkoxy;
V is selected from hydrogen, lower alkyl, lower alkoxy, chlorine, bromine, —NHCOT$^2$ and —NHSO$_2$T$^3$, wherein T$^3$ is lower alkyl, and T$^2$ is selected from hydrogen, lower alkyl, lower alkoxy and amino; and R$^7$ and R$^8$ are each independently selected from hydrogen, lower alkyl, lower alkoxy lower alkoxy carbonyl lower alkyl, lower alkylcarbonyloxy lower alkyl, cyano lower alkyl, lower alkoxycarbonyl lower alkyl, phenyl lower alkyl, cyano lower alkoxycarbonyl lower alkyl, hydroxy lower alkyl, benzoyloxy lower alkyl, phenyl and cyclohexyl.

* * * * *